(12) United States Patent
DeVita et al.

(10) Patent No.: US 8,124,633 B2
(45) Date of Patent: Feb. 28, 2012

(54) HYDROXYMETHYL ETHER HYDROISOINDOLINE TACHYKININ RECEPTOR ANTAGONISTS

(75) Inventors: Robert J. DeVita, Westfield, NJ (US); Sander G. Mills, Scotch Plains, NJ (US); Jinlong Jiang, Scotch Plains, NJ (US); Andrew J. Kassick, Scotch Plains, NJ (US); Jianming Bao, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 266 days.

(21) Appl. No.: 12/593,168

(22) PCT Filed: Apr. 7, 2008

(86) PCT No.: PCT/US2008/004531
§ 371 (c)(1),
(2), (4) Date: Sep. 25, 2009

(87) PCT Pub. No.: WO2008/124143
PCT Pub. Date: Oct. 16, 2008

(65) Prior Publication Data
US 2010/0105747 A1  Apr. 29, 2010

Related U.S. Application Data

(60) Provisional application No. 60/922,663, filed on Apr. 10, 2007.

(51) Int. Cl.
*A61K 31/422* (2006.01)
*C07D 209/02* (2006.01)

(52) U.S. Cl. ......... 514/376; 514/412; 548/225; 548/452
(58) Field of Classification Search .................. None
See application file for complete search history.

(56) References Cited

U.S. PATENT DOCUMENTS

| 6,479,518 | B2  | 11/2002 | Finke et al.       |          |
|-----------|-----|---------|--------------------|----------|
| 6,964,981 | B2  | 11/2005 | Williams et al.    |          |
| 7,217,731 | B2* | 5/2007  | Bunda et al. ...... | 514/415  |
| 7,345,083 | B2* | 3/2008  | Bunda et al. ...... | 514/415  |
| 7,652,058 | B2* | 1/2010  | DeVita et al. ..... | 514/414  |
| 7,683,068 | B2* | 3/2010  | Jiang et al. ...... | 514/255.05 |
| 2005/0165083 | A1 | 7/2005 | Bunda et al.       |          |

FOREIGN PATENT DOCUMENTS

| WO | WO 2005/073191 A2 | 8/2005 |
| WO | WO 2006/060344 A2 | 6/2006 |
| WO | WO 2006/060346 A2 | 6/2006 |

OTHER PUBLICATIONS

Patani et al. [Patani, George A. Bioisoterism: A rational approach in drug design. Chem. Rev. 96 (1996) 3147-3176.*

* cited by examiner

*Primary Examiner* — Kamal Saeed
(74) *Attorney, Agent, or Firm* — Yong Zhao; Valerie J. Camara

(57) ABSTRACT

The present invention is directed to certain hydroxymethyl ether hydroisoindoline compounds which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, LUTS, depression, and anxiety.

19 Claims, No Drawings

HYDROXYMETHYL ETHER HYDROISOINDOLINE TACHYKININ RECEPTOR ANTAGONISTS

CROSS REFERENCE TO RELATED APPLICATIONS

This application is a U.S. National Phase application under 35 U.S.C. §371 of PCT Application No. PCT/US2008/004531, filed Apr. 7, 2008 which claims priority under 35 U.S.C. §119(e) from U.S. Provisional Application Serial No. 60/922,663, filed Apr. 10, 2007.

BACKGROUND OF THE INVENTION

Substance P is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence. In addition to substance P, the known mammalian tachykinins include neurokinin A and neurokinin B. The current nomenclature designates the receptors for substance P, neurokinin A, and neurokinin B as neurokinin-1 (NK-1), neurokinin-2 (NK-2), and neurokinin-3 (NK-3), respectively.

Tachykinin, and in particular substance P, antagonists are useful in the treatment of clinical conditions which are characterized by the presence of an excess of tachykinin, in particular substance P, activity, including disorders of the central nervous system, nociception and pain, gastrointestinal disorders, disorders of bladder function and respiratory diseases.

SUMMARY OF THE INVENTION

The present invention is directed to certain hydroxymethyl ether hydroisoindoline compounds of Formula (I) which are useful as neurokinin-1 (NK-1) receptor antagonists, and inhibitors of tachykinin and in particular substance P. The invention is also concerned with pharmaceutical formulations comprising these compounds as active ingredients and the use of the compounds and their formulations in the treatment of certain disorders, including emesis, urinary incontinence, LUTS, depression, and anxiety.

DETAILED DESCRIPTION OF THE INVENTION

In one embodiment the present invention is directed to compounds of the formula I:

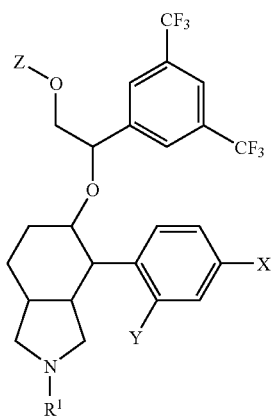

I and pharmaceutically acceptable salts thereof and individual enantiomers and diastereomers thereof, wherein:

$R^1$ is selected from the group consisting of:
(1) hydrogen,
(2) $C_{1-6}$alkyl, which is unsubstituted or substituted with halogen, hydroxyl or phenyl,
(3) cyclopentenone, which is unsubstituted or substituted with hydroxyl,
(4) —(CO)—$C_{1-6}$alkyl,
(5) —(CO)—$NH_2$,
(6) —(CO)—$NHC_{1-6}$alkyl,
(7) —(CO)—$N(C_{1-6}$alkyl$)(C_{1-6}$alkyl$)$,
(8) —(CO)—O—$C_{1-6}$alkyl,
(9) —(CO)—$C_{3-6}$cycloalkyl, and

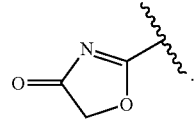

(10)

X is independently selected from the group consisting of:
(1) hydrogen, and
(2) fluorine;
Y is independently selected from the group consisting of:
(1) hydrogen, and
(2) methyl;
Z is independently selected from the group consisting of:
(1) hydrogen,
(2) $C_{1-6}$alkyl, which is unsubstituted or substituted with halogen, hydroxyl or phenyl,
(3) —(CO)—$C_{1-6}$alkyl,
(4) —(CO)-Aryl
(5) —(CO)O—$C_{1-6}$alkyl,
(6) —(CO)—$NH_2$,
(7) —(CO)—$NHC_{1-6}$alkyl, and
(8) —(CO)—$N(C_{1-6}$alkyl$)(C_{1-6}$alkyl$)$,
wherein the alkyl portion of choices (4), (7) and (8) of R1 are optionally substituted with halo, hydroxyl or phenyl.

Within this embodiment, there is a genus of compounds of the Formula Ia and Ib:

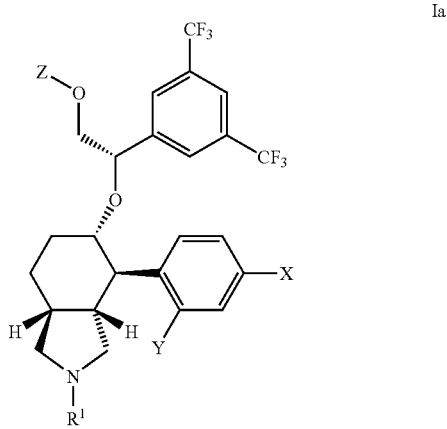

Ia

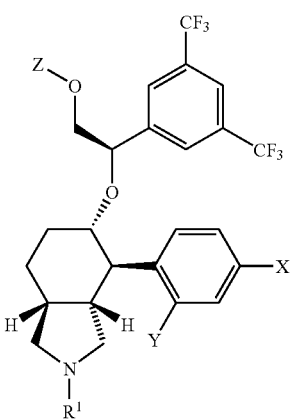

wherein $R^1$, X, Y and Z are defined herein,
and pharmaceutically acceptable salts thereof and individual enantiomers and diastereomers thereof.

Within this embodiment there is sub-genus of compounds of Formulae (I), (Ia) and (Ib) wherein
$R^1$ is selected from the group consisting of:
(1) hydrogen,
(2) $C_{1-3}$alkyl, which is unsubstituted or substituted with hydroxyl or phenyl,
(3) cyclopent-2-en-1-one, which is unsubstituted or substituted with hydroxyl,
(4) —(CO)—$C_{1-3}$alkyl,
(5) —(CO)—$NH_2$,
(6) —(CO)—$NHC_{1-3}$alkyl,
(7) —(CO)—$N(C_{1-3}alkyl)(C_{1-3}alkyl)$, and

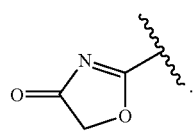

wherein the alkyl portion of choices (4), (6) and (7) of R1 are optionally substituted with halo, hydroxyl or phenyl.

Within this sub-genus there is a class herein $R^1$ is selected from the group consisting of:
(1) hydrogen,
(2) cyclopent-2-en-1-one,
(3) 1,2-oxazol-4(5H)-one,
(4) 2,2-dimethylpropanoyl,
(5) methylpropanoyl,
(6) $CH_3NH$—(CO)—, and
(7) $(CH_3)_2$—N—(CO)—.

Within this class there is a sub-class wherein $R^1$ is hydrogen.

Within this class there is another sub-class wherein $R^1$ is:

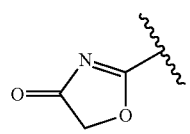

Within this class there is another sub-class wherein $R^1$ is:

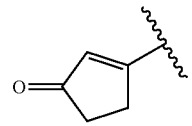

Within this class there is a sub-class wherein $R^1$ is $CH_3NH$—(CO)—, or $(CH_3)_2$—N—(CO)—.

Within this embodiment there is a genus of compounds wherein Z is selected from the group consisting of
(1) hydrogen,
(2) $C_{1-3}$alkyl, which is unsubstituted or substituted with halogen, hydroxyl or phenyl,
(3) —(CO)-phenyl, and
(4) —(CO)O-methyl.

Within this embodiment there is sub-genus of compound of Formulae (I), (Ia) and
(Ib) wherein X is hydrogen. Within this embodiment there is sub-genus of compound of Formulae (I), (Ia) and (Ib) wherein X is fluorine.

Within this embodiment there is a genus of compounds of formula Ia or Ib:

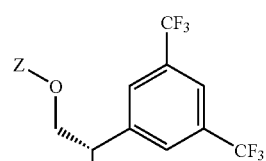

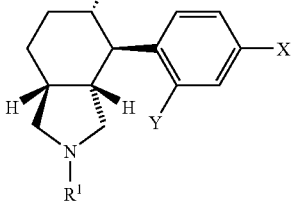

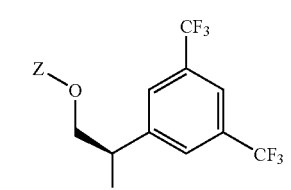

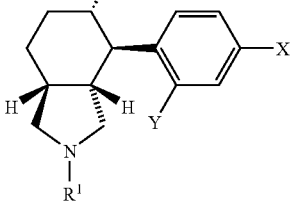

or a pharmaceutically acceptable salt thereof and individual enantiomers and diastereomers thereof wherein
$R^1$ is selected from the group consisting of:
(1) hydrogen,
(2) cyclopent-2-en-1-one,
(3) 1,2-oxazol-4(5H)-one, (4) 2,2-dimethylpropanoyl,
(5) methylpropanoyl,
(6) CH$_3$NH—(CO)—,
(7) (CH$_3$)$_2$—N—(CO)—, and

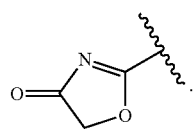
(8)

X is independently selected from the group consisting of:
  (1) hydrogen, and
  (2) fluorine;
Y is independently selected from the group consisting of:
  (1) hydrogen, and
  (2) methyl;
Z is independently selected from the group consisting of:
  (1) hydrogen,
  (2) C$_{1-6}$alkyl, which is unsubstituted or substituted with halogen, hydroxyl or phenyl,
  (3) —(CO)—C$_{1-6}$alkyl,
  (4) —(CO)-Aryl,
  (5) —(CO)O—C$_{1-6}$alkyl,
  (6) —(CO)—NH$_2$,
  (6) —(CO)—NHC$_{1-6}$alkyl, and
  (7) —(CO)—N(C$_{1-6}$alkyl)(C$_{1-6}$alkyl), Within this genus there is a sub-genus of compounds wherein Z is selected from the group consisting of
  (1) hydrogen,
  (2) C$_{1-3}$alkyl, which is unsubstituted or substituted with halogen, hydroxyl or phenyl,
  (3) —(CO)-phenyl, and
  (4) —(CO)O-methyl.

Specific embodiments of the present invention include a compound which is selected from the group consisting of the subject compounds of the Examples herein and pharmaceutically acceptable salts thereof and individual enantiomers and diastereomers thereof.

Within this embodiment there is sub-genus of compound of Formulae (I), (Ia) and (Ib) wherein Y is hydrogen. Within this embodiment there is another sub-genus of compound of Formulae (I), (Ia) and (Ib) wherein Y is methyl.

Specific embodiments of the present invention include a compound which is selected from the group consisting of the subject compounds of the Examples herein and pharmaceutically acceptable salts thereof and individual enantiomers and diastereomers thereof.

Within this embodiment there is sub-genus of compound of Formulae (I), (Ia) and (Ib) wherein Z is hydrogen. Within this embodiment there is another sub-genus of compound of Formulae (I), (Ia) and (Ib) wherein Z is methyl.

Specific embodiments of the present invention include a compound which is selected from the group consisting of the subject compounds of the Examples herein and pharmaceutically acceptable salts thereof and individual enantiomers and diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

There are several acceptable methods of naming the compounds discussed herein.

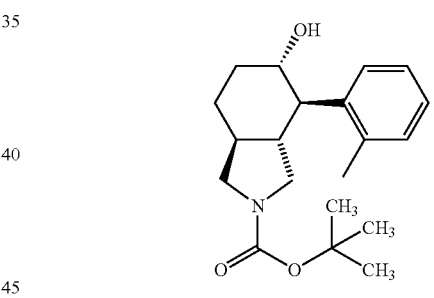

For example, the above compound can be named either as "(3aR,4R,5S,7aR) tert-butyl-5-hydroxy-4-(2-methylphenyl)octahydro-2H-isoindole-2-carboxylate" or "tert-butyl (3aR,4R,5S,7aR)-5-hydroxy-4-phenyloctahydro-2H-isoindole-2-carboxylate". The core structure may be generally referred to as octahydroisoindole, hexahydroisoindoline, perhydroisoindoline, hydroisoindoline, or hydroisoindole compounds.

As appreciated by those of skill in the art, halo or halogen as used herein are intended to include fluoro, chloro, bromo and iodo. Similarly, C$_{1-6}$, as in C$_{1-6}$alkyl is defined to identify the group as having 1, 2, 3, 4, 5 or 6 carbons in a linear or branched arrangement, such that C$_{1-8}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual diastereomers thereof.

The compounds of the present invention are useful in the prevention and treatment of a wide variety of clinical conditions which are characterized by the presence of an excess of tachykinin, in particular substance P, activity. Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculoskeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynecological pain, for example, dysmenorrhea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritus and sunburn; allergies such as eczema and rhinitis; hypersensitivity disorders such as poison ivy; ophthalmic diseases such as conjunctivitis, vernal conjunctivitis, and the like; ophthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorders; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia, frequent urination, urinary incontinence and LUTS, including the prevention or treatment of overactive bladder with symptoms of urge urinary incontinence, urgency, and frequency; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

As used herein, the term "urinary incontinence" is intended to include a range of conditions including urge incontinence, stress incontinence, overflow incontinence, functional incontinence, neurogenic incontinence, post-prostatectomy incontinence, urinary frequency, urinary urgency, nocturia, enuresis, and related conditions in mammalian subjects. In more detailed embodiments, the lower urinary tract disorder, or targeted symptoms for treatment arising therefrom, may include overactive bladder, including neurogenic and non-neurogenic overactive bladder, interstitial cystitis, prostatitis, prostadynia, and benign prostatic hyperplasia. In further embodiments, the methods and compositions of the invention are effective for preventing or treating excessive micturition in subjects suffering from lower urinary tract disorders.

The compounds of the present invention are also of value in the treatment of a combination of the above conditions, in particular in the treatment of combined post-operative pain and post-operative nausea and vomiting.

The compounds of the present invention are particularly useful in the prevention or treatment of emesis, including acute, delayed or anticipatory emesis, such as emesis induced by chemotherapy, radiation, toxins, pregnancy, vestibular disorders, motion, surgery, migraine, and variations in intercranial pressure. For example, the compounds of the present invention are of use optionally in combination with other antiemetic agents for the prevention of acute and delayed nausea and vomiting associated with initial and repeat courses of moderate or highly emetogenic cancer chemotherapy, including high-dose cisplatin. Most especially, the compounds of the present invention are of use in the treatment of emesis induced by antineoplastic (cytotoxic) agents, including those routinely used in cancer chemotherapy, and emesis induced by other pharmacological agents, for example, rolipram. Examples of such chemotherapeutic agents include alkylating agents, for example, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics. Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177-203, especially page 188. Commonly used chemotherapeutic agents include cisplatin, dacarbazine (DTIC), dactinomycin, mechlorethamine, streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163-172].

A further aspect of the present invention comprises the use of a compound of the present invention for achieving a chronobiologic (circadian rhythm phase-shifting) effect and alleviating circadian rhythm disorders in a mammal. The present invention is further directed to the use of a compound of the present invention for blocking the phase-shifting effects of light in a mammal.

A further aspect of the present invention comprises the use of a compound of the present invention in the treatment of Lower urinary tract symptoms (LUTS). LUTS in men include, but are not, restricted to a complex of obstructive (voiding) and irritative (storage or filling) symptoms, which include increased frequency, nocturia, poor urinary stream and hesitancy or delay in starting urinary flow. LUTS are recognized as arising from changes in urethral resistance induced by the enlarging prostate as well as contraction of the prostatic smooth muscle. The resulting increase in urethral resistance restricts the outflow of urine and causes secondary changes are induced in the bladder. A characteristic pattern of unstable bladder contractions, also known as irritable bladder, is often observed in men with morphological BPH.

The present invention is further directed to the use of a compound of the present invention or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of the present invention or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The particularly preferred embodiments of the instant invention are the treatment of emesis, urinary incontinence, depression or anxiety by administration of the compounds of the present invention to a subject (human or animal) in need of such treatment.

The present invention is directed to a method for the manufacture of a medicament for antagonizing the effect of substance P at its receptor site or for the blockade of neurokinin-1 receptors in a mammal comprising combining a compound of the present invention with a pharmaceutical carrier or diluent.

The present invention is further directed to a method for the manufacture of a medicament for the treatment of a physiological disorder associated with an excess of tachykinins in a mammal comprising combining a compound of the present invention with a pharmaceutical carrier or diluent.

The present invention also provides a method for the treatment or prevention of physiological disorders associated with an excess of tachykinins, especially substance P, which method comprises administration to a patient in need thereof of a tachykinin reducing amount of a compound of the present invention or a composition comprising a compound of the present invention.

As used herein, the term "treatment" or "to treat" refers to the administration of the compounds of the present invention to reduce, ameliorate, or eliminate either the symptoms or underlying cause of the noted disease conditions, in a subject (human or animal) that suffers from that condition or displays clinical indicators thereof.

The term "prevention" or "to prevent" refers to the administration of the compounds of the present invention to reduce, ameliorate, or eliminate the risk or likelihood of occurrence of the noted disease conditions, in a subject (human or animal) susceptible or predisposed to that condition.

The compounds of this invention are useful for antagonizing tachykinins, in particular substance P in the treatment of gastrointestinal disorders, central nervous system disorders, inflammatory diseases, pain or migraine and asthma in a mammal in need of such treatment. This activity can be demonstrated by the following assays.

Receptor Expression in COS: To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (1131, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

Stable Expression in CHO: To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer supplemented with 0.625 mg/ml Herring sperm DNA at 300 V and 950 uF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

Assay Protocol using COS or CHO: The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter. The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of 3H-myoinositol by overnight incubation. The extracellular radioactivity is removed by washing with phosphate buffered saline. LiCl is added to the well at final concentration of 0.1 mM with or without the test compound, and incubation is continued at 37° C. for 15 mM. Substance P is added to the well at final concentration of 0.3 nM to activate the human NK1R. After 30 min of incubation at 37° C., the media is removed and 0.1 N HCl is added. Each well is sonicated at 4° C. and extracted with $CHCl_3$/methanol (1:1). The aqueous phase is applied to a 1 ml Dowex AG 1×8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

In particular, the intrinsic tachykinin receptor antagonist activities of the compounds of the present invention may be demonstrated by this assay. The compounds of the invention have activity in the aforementioned assay in the range of 0.05 nM to 10 µM. The Examples hereinunder were found to have the following activity:

| Example | IC50 (nM) |
| --- | --- |
| 1 | — |
| 2 | 0.04 |
| 3 | 0.06 |
| 4 | 0.1 |
| 5 | 0.06 |
| 6 | 0.03 |
| 7 | 0.08 |
| 8 | 0.03 |
| 9 | 0.09 |
| 10 | 0.03 |
| 11 | 0.03 |
| 12 | 0.07 |
| 13 | 0.06 |
| 14 | 0.46 |
| 15 | 17 |
| 16 | 0.35 |
| 17 | — |
| 18 | — |
| 19 | — |
| 20 | — |
| 21 | 55 |
| 22 | 2.2 |
| 23 | 2.1 |

-continued

| Example | IC50 (nM) |
|---|---|
| 24 | 45 |
| 25 | 3.1 |
| 26 | 59 |
| 27 | 47% at 0.1 nM |

The activity of the present compounds may also be demonstrated by the assay disclosed by Lei, et al., *British J. Pharmacol.*, 105, 261-262 (1992).

According to a further or alternative aspect, the present invention provides a compound of the present invention for use as a composition that may be administered to a subject in need of a reduction of the amount of tachykinin or substance P in their body.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives.

Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

The compositions containing compounds of the present invention may be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples in the pharmacy arts of unit dosage forms.

The compositions containing compounds of the present invention may also be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individuals body in a therapeutically useful form and therapeutically effective amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The term "therapeutically effective amount" refers to a sufficient quantity of the compounds of the present invention, in a suitable composition, and in a suitable dosage form to treat or prevent the noted disease conditions.

The compounds of the present invention may be administered in combination with another substance that has a complimentary effect to the tachykinin and substance P inhibitors of the present invention.

Accordingly, in the prevention or treatment of emesis, a compound of the present invention may be used in conjunction with other anti-emetic agents, especially 5HT$_3$ receptor antagonists, such as ondansetron, granisetron, tropisetron, palenosetron and zatisetron, a corticosteroid, such as dexamethasone, or GABA$_B$ receptor agonists, such as baclofen. Likewise, for the prevention or treatment of migraine a compound of the present invention may be used in conjunction with other anti-migraine agents, such as ergotamines or 5HT$_1$ agonists, especially sumatriptan, naratriptan, zolmatriptan or rizatriptan.

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, 5-HT$_{1A}$ agonists or antagonists, especially 5-HT$_{1A}$ partial agonists, corticotropin releasing factor (CRF) antagonists, and pharmaceutically acceptable salts thereof. For the treatment or prevention of eating disorders, including obesity, bulimia nervosa and compulsive eating disorders, a compound of the present invention may be used in conjunction with other anorectic agents. It will be appreciated that for the treatment or prevention of pain or nociception or inflammatory diseases, a compound of the present invention may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent.

For the treatment of urinary incontinence and LUTS, a compound of the invention may be used in combination with a β3 adrenergic receptor (β3AR) agonist (β3 agonist), and/or an anti-muscatinic and optionally an alpha-1 adrenergic antagonist, or a steroid type II 5-alpha-reductase inhibitor.

For purposes of this specification the β3 agonist is intended to include N-[4-[2-[[2-hydroxy-2-(pyridin-3-yl)ethyl]amino]ethyl] phenyl]-4-[4-(3-cyclopentylpropyl)-5-tetrazolon-1-yl]benzenesulfonamide; and 2 N-[4-[2-[[2-hydroxy-2-(pyridin-3-yl)ethyl]amino]ethyl] phenyl]-4-[4-[4-(trifluoromethyl)phenyl]thiazol-2-yl]benzenesulfonamide. Appropriate daily amounts of the (β3 agonist include 10 mg, 25, mg, 50 mg, 100 mg, 125 mg, 200 mg, 250 mg and 375 mg. These beta 3 agonists are discussed and may be prepared as disclosed in U.S. Pat. No. 5,561,142 and U.S. Pat. No. 6,011,048, which are hereby incorporated by reference.

For purposes of this specification, anti-muscarinic agents included, but are not limited to tolterodine, oxybutynin, trospium, vamicamide, solifenacin, propiverine, S-oxybutynin, temiverine, sanctura, staybla, fesoterodine, SVT40776, 202405 by GlaxoSmithKline, TD6301, RBX9841, DDP200, and PLD179. See, for example, U.S. Pat. No. 5,382,600; U.S. Pat. No. 3,176,019; U.S. Pat. No. 3,480,626; U.S. Pat. No. 4,564,621; U.S. Pat. No. 5,096,890; U.S. Pat. No. 6,017,927; U.S. Pat. No. 6,174,896; U.S. Pat. No. 5,036,098; U.S. Pat. No. 5,932,607; U.S. Pat. No. 6,713,464; U.S. Pat. No. 6,858,650; and DD 106643. See also, U.S. Pat. No. 6,103,747; U.S. Pat. No. 6,630,162; U.S. Pat. No. 6,770,295; U.S. Pat. No. 6,911,217; U.S. Pat. No. 5,164,190; U.S. Pat. No. 5,601,839; U.S. Pat. No. 5,834,010; U.S. Pat. No. 6,743,441; WO2002000652; WO200400414853. These also include trospium chloride, darifenacin and imidafenacin (KRP-197). As will be appreciate by those of skill in the art, these drugs may be administered orally or topically in standard or extended release forms, such as extended release tolterodine, extended release oxybutynin and transdermal oxybutynin.

Within the aspect of the invention discussed above, there is a genus wherein the anti-muscarinic agent is selected from tolterodine, oxybutynin, trospium, vamicamide, solifenacin, propiverine, S-oxybutynin, temiverine, sanctura, staybla, fesoterodine, SVT40776, 202405 by GlaxoSmithKline, TD6301, RBX9841, DDP200, and PLD179.

Within the aspect of the invention discussed above, there is a genus wherein the anti-muscarinic agent is selected from the group consisting of trospium chloride, darifenacin and imidafenacin.

Within the aspect of the invention discussed above, there is a genus wherein the anti-muscarinic agent is selected from the group consisting of extended release tolterodine, extended release oxybutynin and transdermal oxybutynin.

For purposes of this specification the 5-alpha reductase inhibitor includes, but is not limited to finasteride, dutasteride, turosteride and episteride.

By the term "finasteride" as used here is meant the compound as designated by 4-azaandrost-1-ene-17-carboxamide, N-(1,1-dimethylethyl)-3-oxo-,(5α,17β). FDA approved doses for finasteride are 1 mg and 5 mg, once a day.

By the term "dutasteride" as used herein is meant the compound as designated by (5α,17β)-N-{2,5bis(trifluoromethyl)phenyl}-3-oxo-4-azaandrost-1-ene-17-carboxamide. FDA approved doses for finasteride are 1 mg and 5 mg, once a day. The FDA approved dose for dutasteride is 0.5 mg, once a day. The FDA approved dose for dutasteride is 0.5 mg, once a day.

For purposes of this specification the alpha-adrenergic receptor antagonist is selected from amsulosin, terazosin, doxazosin, alfuzosin, indoramin and prazosin.

By the term "amsulosin" (e.g. Flomax or tamsulosin hydrochloride) as used herein is meant the compound designated as (−)-(R)-5-[2-[[2-(O-ethoxyphenoxy)ethyl]amino]propyl]-2-methoxybenzenesulfonamide and salts, hydrates and solvates thereof. Amsulosin is disclosed in U.S. Pat. No. 4,703,063 and claimed in U.S. Pat. No. 4,987,152 as being useful in treating lower urinary tract dysfunction. FDA approved doses include 0.4 mg once a day for tamsulosin hydrochloride.

By the term "terazosin" as used herein is meant the compound 1-(4-amino-6,7-dimethoxy-2quinazolinyl)-4-[(tetrahydro-2-furoyl)carbonyl]piperazine and salts, hydrates and solvates thereof. Terazosin is disclosed in U.S. Pat. No. 4,251,532. FDA approved doses include 1, 2, 5 and 10 mg once a day for terazosin hydrochloride.

By the term doxazosin as used herein is meant the compound I-(4-amino-6,7-dimethoxy-2-quinazolinyl)-4-[(2,3-dihydro-1,4-benzodioxin-2-yl)carbonyl]-piperazine and salts, hydrates and solvates thereof. Doxazosin is disclosed in U.S. Pat. No. 4,188,390. FDA approved doses include 1, 2, 4 and 8 mg once a day for doxazosin mesylate.

By the term "alfuzosin" (e.g. Uroxatral) as used herein is meant the compound N-[3-[(4-amino-6,7-dimethoxy-2-quinazolinyl)methylamino]propyl]tetrahydro-2-furancarboxamide and salts, hydrates and solvates thereof. Alfuzosin is disclosed in U.S. Pat. No. 4,315,007. FDA approved doses include 10 mg once a day for alfuzosin hydrochloride.

By the term "indoramin" as used herein is meant the compound N-[[1-[2-(1H-indol-3-yl)ethyl]-4-piperidinyl]benzamine. Indoramin is disclosed in U.S. Pat. No. 3,527,761.

By the term "prazosin" as used herein is meant a compound of the formula 1-(4-amino-6,7-dimethoxy-2-quinazolinyl)-4-(2-furanylcarbonyl)piperazine. and solvates thereof. Prazosin is disclosed in U.S. Pat. No. 3,511,836. FDA approved doses include 1, 2 and 5 mg once a day for prazosin hydrochloride.)

It will be appreciated that when using any combination described herein, both the compound of the present invention and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a tablet, then within one hour, the second active component should be administered, either in the same type of dosage form, or another dosage form which provides effective delivery of the medicament.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of the conditions associated with an excess of tachykinins, a suitable dosage level of the compounds of the present invention, or pharmaceutically acceptable salts thereof, is about 0.001 to 50 mg/kg per day, in particular about 0.01 to about 25 mg/kg, such as from about 0.05 to about 10 mg/kg per day. The dosage range will generally be about 0.5 to 1000 mg per patient per day, which may be administered in single or multiple doses. Preferably, the dosage range will be about 0.5 mg to 500 mg per patient per day; more preferably about 0.5 mg to 200 mg per patient per day; and even more preferably about 5 mg to 50 mg per patient per day. Specific dosages of the compounds of the present invention, or pharmaceutically acceptable salts thereof, for administration include 1 mg, 5 mg, 10 mg, 30 mg, 100 mg, and 500 mg.

Pharmaceutical compositions of the present invention may be provided in a formulation comprising about 0.5 mg to 1000 mg active ingredient; more preferably comprising about 0.5 mg to 500 mg active ingredient; or 0.5 mg to 250 mg active ingredient; or 1 mg to 100 mg active ingredient. Specific pharmaceutical compositions for treatment or prevention of excess tachykinins comprise about 1 mg, 5 mg, 10 mg, 30 mg, 100 mg, and 500 mg of active ingredient.

Several methods for preparing the compounds of this invention are illustrated in the following Examples. Starting materials and the requisite intermediates are in some cases commercially available, or can be prepared according to literature procedures or as illustrated herein. All NMR spectra were obtained on instrumentation at field strength of 400 or 500 MHz.

EXAMPLE 1

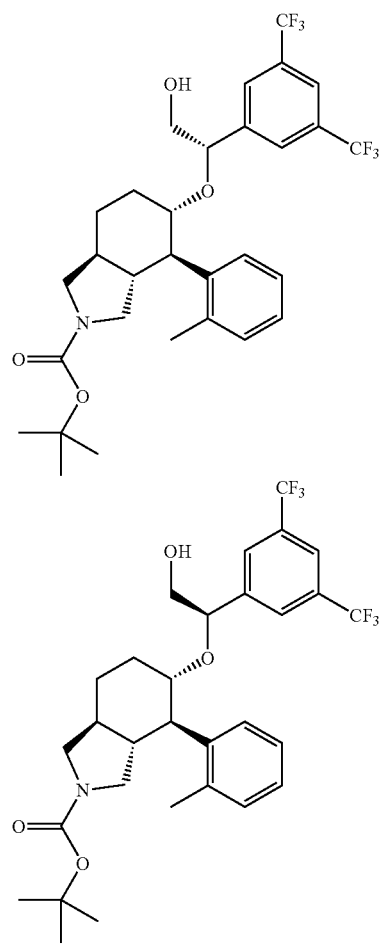

tert-Butyl (3aR,4R,5S,7aS)-5-{(1S)-1-[3,5-bis(trifluoromethyl)phenyl]-2-hydroxyethoxy}-4-(2-methylphenyl)octahydro-2H-isoindole-2-carboxylate and tert-butyl (3aR,4R,5S,7aS)-5-{(1R)-1-[3,5-bis(trifluoromethyl)phenyl]-2-hydroxyethoxy}-4-(2-methylphenyl)octahydro-2H-isoindole-2-carboxylate (mixture of two isomers)

Step A: N-Methoxy-N-methyl-2-(2-methylphenyl)acetamide

To a solution of (2-methylphenyl)acetic acid in dry methylene chloride (16.7 g, 108.4 mmol) under nitrogen atmosphere was added N,O-dimethylhydroxylamine (13.8 g, 141.5 mmol), triethylamine (20 mL, 143.8 mmol), 4-dimethylaminopyridine (DMAP, 14.2 g, 119.3 mmol) and EDC (27 g, 140.6 mmol). The reaction mixture was stirred at RT for 2 hr then transferred to a separation funnel. The mixture was washed consecutively with 2 N aq. HCl, brine, saturated aq. NaHCO$_3$ and brine. The organic layer was dried over MgSO$_4$, filtered and the solvent evaporated under vacuum to give 21 g of the crude title compound which was used without further purification. $^1$H-NMR (CDCl$_3$): δ: 7.20 (4H, m), 3.80 (2H, s), 3.65 (2H, s), 3.65 (3H, s), 2.34 (3H, m).

Step B: 1-(2-Methylphenyl)but-3-en-2-one

To a solution of vinylmagnesium bromide (220 mL, 1.0 M, 220 mmol) in 100 mL THF, was added dropwise under nitrogen atmosphere at 0° C. a solution of 2-(2-methylphenyl)-N-methoxy-N-methylacetamide (Step A, 21 g, 106.6 mmol) in ~150 mL dry ether. The reaction mixture was stirred at 0° C. for 0.5 hr then poured slowly into an ice/2N aq HCl (300 mL) mixture. The resulting mixture was diluted with ether, transferred to a separation funnel. The organic layer was separated, washed with brine, dried over MgSO$_4$, filtered and the solvent evaporated under vacuum to give 14.2 g of the crude title compound which was used without further purification. $^1$H-NMR (CDCl$_3$): δ: 7.15-7.25 (4H, m), 6.47 (1H, dd, J$_1$=14.2 Hz, J$_2$=11 Hz), 6.35 (1H, d, J=14.2 Hz), 5.86 (1H, d, J=11 Hz), 3.83 (2H, s), 2.28 (3H, s).

Step C: Triethyl {[(1Z)-1-(2-methylbenzylidene)prop-2-en-1-yl]oxy}silane and triethyl {[(1E)-1-(2-methylbenzylidene)prop-2-en-1-yl]oxy}silane To a solution of 1-(2-methylphenyl)but-3-en-2-one (Step B, 14.2 g, 86.6 mmol, 1 equiv.) and diisopropylethylamine (24.1 mL, 138.6 mmol, 1.6 equiv.) in a mixture of solvents of acetonitrile, THF and toluene (200 mL:100 mL:25 mL) was added chlorotriethylsilane (23.4 mL, 1.6 equiv. 138.6 mmol) via a separation funnel at room temperature. The resulting solution was allowed to stir overnight at room temperature. The reaction mixture was quenched with 185 mL 2% ammonium chloride (4 g). The organic layer was separated and washed with 185 mL water, dried over anhydrous MgSO4 and concentrated under vacuum to give 20.5 g of the crude title compounds which were used without further purification. $^1$H-NMR (CDCl$_3$): δ: 7.68 (1H, d, J=7.8 Hz), 7.15 (3H, m), 6.32 (1H, dd, J$_1$=13.2 Hz, J$_2$=8.5 Hz), 5.82 (1H, s), 5.55 (1H, d, J=13.2 Hz), 5.18 (1H, d, J=8.5 Hz).

Step D: Diethyl (1S,2S)-3-(2-methylphenyl)-4-[(triethylsilyl)oxy]cyclohex-4-ene-1,2-dicarboxylate, diethyl (1R,2R)-3-(2-methylphenyl)-4-[(triethylsilyl)oxy]cyclohex-4-ene-1,2-dicarboxylate, diethyl (1S,2R)-3-(2-methylphenyl)-4-[(triethylsilyl)oxy]cyclohex-3-ene-1,2-dicarboxylate and diethyl (1R,2S)-3-(2-methylphenyl)-4-[(triethylsilyl)oxy]cyclohex-3-ene-1,2-dicarboxylate To a solution of 1E and 1Z-{[1-(2-methylbenzylidene)prop-2-en-1-yl]oxy}triethylsilanes (Step C, 14 g, ~80% pure, 133.1 mmol, 1 equiv.) and diethyl (2E)-but-2-enedioate (6.5 mL, 6.85 g, 39.6 mmol) in 100 mL xylenes under nitrogen atmosphere was heated at 160° C. for 5 hr then cooled to RT. The solvent was evaporated under vacuum to give an oil which was used without further purification.

Step E: Racemic diethyl (1S,2S,3R)-3-(2-methylphenyl)-4-oxocyclohexane-1,2-dicarboxylate and diethyl (1R,2R,3S)-3-(2-methylphenyl)-4-oxocyclohexane-1,2-dicarboxylate To a solution of the above intermediate (Step D) in acetonitrile (150 mL) was added hydrochloric acid (6 N, 10 mL). The resulting mixture was stirred at RT for 24 hr, and the volatiles were removed under vacuum. The crude oil was dissolved in 200 mL ethyl acetate, and the solution was washed with brine, dried over anhydrous magnesium sulfate. The magnesium salt was filtered off and the solvent was evaporated under vacuum to give 18.2 g of the title compounds which were purified by column chromatograph (5:1 hexane:ethyl acetate). $^1$H-NMR (CDCl$_3$): δ: 7.32 (1H, d, J=7.8 Hz), 7.25 (1H, m), 7.14 (2H, m), 4.15 (2H, m), 3.85-3.70 (3H, m), 3.13 (1H, t, J=12.9 Hz), 2.85 (2H, m), 2.33 (3H, s), 2.15 (2H, m), 1.58-1.72 (2H, m), 1.26 (3H, t, J=7.2 Hz), 0.75 (3H, t, J=7.2 Hz).

Step F: Racemic diethyl (1S,2S,3R,4S)-4-hydroxy-3-(2-methylphenyl)cyclohexane-1,2-dicarboxylate and diethyl (1R,2R,3S,4R)-4-hydroxy-3-(2-methylphenyl)cyclohexane-1,2-dicarboxylate To a solution of lithium tri-tertial-butoxyaluminum hydride (66 mL, 1 M, 66 mmol) in 150 mL THF was added a solution of the intermediate of step E (15.2 g, 45.1 mmol) in 75 mL THF under nitrogen atmosphere at –40° C. was added via syringe. The resulting mixture was stirred at –40° C. for 2 hr then at RT for 2 hr. The reaction mixture was carefully quenched by addition of 15 mL water and 30 mL 2 N hydrochloric acid. The emulsion was diluted with ethyl acetate and the mixture was stirred for 1 hr. The solid was then filtered through celite. The filtrate was dried (MgSO$_4$) and the solvent evaporated under vacuum to give the crude title compounds which were purified by column chromatography to afford 13 g solid. $^1$H-NMR (CDCl$_3$): δ: 7.32 (1H, d, J=9.6 Hz), 7.25 (1H, m), 7.14 (2H, m)), 4.13 (2H, m), 3.87-3.65 (2H, m), 3.14 (1H, t, J=10.3 Hz), 2.86 (2H, m), 2.35 (3H, s), 2.25 (2H, m), 1.78-1.58 (2H, m), 1.23 (3H, t, J=7.1 Hz).

Step G: Diethyl (1S,2S,3R,4S)-4-hydroxy-3-(2-methylphenyl)cyclohexane-1,2-dicarboxylate 13 g of the racemic mixture of diethyl (1S,2S,3R,4S)-3-(4-fluorophenyl)-4-hydroxycyclohexane-1,2-dicarboxylate and diethyl (1R,2R,3S,4R)-3-(4-fluorophenyl)-4-hydroxycyclohexane-1,2-dicarboxylate (step F) was separated by preparative chiral HPLC using CHIRACEL AD column eluting with hexanes/i-PrOH (9/1) to afford 6 g of the desired first eluting isomer diethyl (1S,2S,3R,4S)-3-(4-fluorophenyl)-4-hydroxycyclohexane-1,2-dicarboxylate.

Step H: (1S,2R,3R,4S)-3,4-Bis(hydroxymethyl)-2-(2-methylphenyl)cyclohexanol

To a solution of diethyl (1S,2S,3R,4S)-4-hydroxy-3-(2-methylphenyl)cyclohexane-1,2-dicarboxylate (Step G, 64.1 g, 192 mmol) in 250 mL THF under nitrogen atmosphere was slowly added LiBH$_4$ powder (16.7 g, 767 mmol, excess) at 0° C. The resulting mixture was heated at 75° C. for 12 hr then cooled to RT. The reaction mixture was carefully quenched by addition of 30 mL water at 0° C., then 30 mL 2 N hydrochloric acid. The organic layer was separated and the aqueous was extracted with EtOAc. The combined organic extracts were washed with aqueous NaHCO$_3$, dried over Na$_2$SO$_4$, filtered and the solvent evaporated under vacuum to give 43.7 g of the crude title compound which was used without further purification. $^1$H-NMR (CDCl$_3$): δ: 7.30-7.13 (4H, m), 3.93-3.68 (3H, m), 3.53 (1H, dd, J$_1$=11.2 Hz, J$_2$=2.3 Hz), 3.27 (1H, dd, J$_1$=11.2 Hz, J$_2$=5.1 Hz), 2.85 (1H, t, J=10.5 Hz), 2.39 (3H, s), 2.19 (1H, m), 1.86 (3H, bs), 1.67 (2H, m), 1.55 (1H, m), 1.45 (1H, m).

Step I: [(1S,2R,3R,4S)-4-Hydroxy-3-(2-methylphenyl)cyclohexane-1,2-diyl]bis(methylene) dipropane-1-sulfonate To a solution of (1S,2R,3R,4S)-3,4-Bis(hydroxymethyl)-2-(2-methylphenyl)cyclohexanol (Step H, 43.7 g, 175 mmol) in 100 mL methylene chloride and 100 mL acetonitrile was added propanesulfonyl chloride (44.9 mL, 402 mmol) and 2,6-lutidine (61.0 mL, 524 mmol) at room temperature. The reaction mixture was stirred at room temperature for 24 hr and was monitored by LC-MS (M$^+$+23=485 for bis-sulfonate and M$^+$+23=379 for monosulfonate). LC-MS showed some mono-sulfonate. 0.5 equivalent of n-propanesulfonyl chloride (9.8 mL, 88 mmol) and 0.6 equivalent of 2,6-lutidine (12.2 mL, 104.8 mmol) were added. The resultant mixture was stirred for 17 hr. The reaction was quenched with 2 N HCl aqueous and diluted with ether. The organic layer was separated, and was washed with brine. The aqueous was extracted with ether. The combined organic extract was washed with brine, dried over MgSO4. The dry agent was removed by filtration, and the filtrate was concentrated to give an oil, which was used without further purification. M+ +23: 485.34.

Step J: (3aR,4R,5S,7aS)-2-benzyl-4-(2-methylphenyl)octahydro-1H-isoindol-5-ol

In a pressure tube was placed a solution of crude [(1S,2R,3R,4S)-4-hydroxy-3-(2-methylphenyl)cyclohexane-1,2-diyl]di(methylene) dipropanesulfonate (Step 1.85 g, 184 mmol) in ~120 mL ethanol and benzylamine (70.2 mL, 643 mmol). The pressure tube was sealed and heated at 140° C. in an oil bath for 3 hr. The tube was cooled to RT and opened. LC-MS showed that the reaction was completed. The resulting mixture was diluted with 180 mL methanol and 100 mL 5 N aq. NaOH. The ethanol, some of water and benzylamine were removed under vacuum. The residue was dissolved in ethyl acetate and diluted with water. The organic layer was separated and the aqueous was extracted with ethyl acetate. The combined organic layers were dried over MgSO$_4$, filtered and the solvent was evaporated under vacuum. The combined organics were concentrated, and the residue oil was purified by column chromatography (1:9 methanol:ethyl acetate. $^1$H-NMR (CDCl$_3$): δ: 7.35-7.10 (9H, m), 3.81-3.62 (3H, m), 2.94 (1H, t, J=8.1 Hz), 2.83 (1H, t, J=10.0 Hz), 2.52 (2H, m), 2.40 (1H, t, J=10.0 Hz), 2.36 (3H, s), 2.20 (1H, m), 2.02-1.85 (3H, m), 1.60 (1H, m), 1.36 (1H, m). M+ +1: 322.19.

Step K: tert-Butyl (3aR,4R,5S,7aS)-5-hydroxy-4-(2-methylphenyl)octahydro-2H-isoindole-2-carboxylate To a solution of (3aR,4R,5S,7aS)-2-benzyl-5-hydroxy-4-(2-methylphenyl)octahydro-1H-isoindole (Step J, 43.5 g) in 150 mL EtOH was added Pd(OH)$_2$—C (14.25 g, 20.3 mmol, 20% by weight). The reaction mixture was hydrogenated at 50 PSI for 16 hr at RT. The catalyst was filtered, and the solvent of the filtrate was evaporated under vacuum to give the title compound (31.0 g) which was directly used in the next step without purification. M+ +1: 232.30. The hydroisoindoline (31 g, 134 mmol) was dissolved in methylene chloride (300 mL), and the solution was stirred with di(t-butyl)bicarbonate (43.9 g, 201 mmol) at room temperature overnight. The solvent was removed and the crude material was purified by silica gel column chromatography (2:1 hexane:ethyl acetate) to give 34.0 g of the desired compound. $^1$H-NMR (CDCl$_3$): δ: 7.32-7.11 (4H, m), 3.90-3.73 (1H, m), 3.68, 3.60 (1H, two multiplets), 3.25, 3.15 (1H, two multiplets), 2.96, 2.72 (4H, two multiplets), 2.41, 2.37 (3H, two singlets), 2.26 (1H, m), 2.11-1.80 (3H, m), 1.62 (1H, m), 1.62 (3H, s), 1.45, 1.42 (6H, two singlets). M+ +1−57+1: 276.11.

Step L: 4-Methylbenzenesulfonyl azide

A solution d sodium azide (3.19 g, 44.6 mmol) in 15 mL water is placed in a 250 mL Erlenmeyer flask and was diluted with 40 mL 90% aqueous ethanol. To this solution was added with stirring a warm (45° C.) solution of 4-methanesulfonyl chloride (8.5 g, 44.6 mL) in 40 mL ethanol. After the mixture was stirred at room temperature for 2.5 hr, most of the solvent was removed under vacuum at 35° C. The residue was dissolved in ethyl acetate and water, and was transferred into a separation funnel. The organic layer was separated, washed with brine, dried over MgSO4 and the solvent was removed (8.0 g). $^1$H-NMR (CDCl$_3$): δ: 7.86 (2H, d, J=8.2 Hz), 7.41 (2H, d, J=8.3 Hz), 2.46 (3H, s).

Step M: Ethyl 3,5-bis(trifluoromethyl)phenylacetate

To a solution of 3,5-bis(trifluoromethyl)phenylacetic acid (24.65 g, 91 mmol) in dichloromethane (150 mL), was added 200 proof ethanol (10.63 mL, 181 mmol), EDC (34.7 g, 181 mmol) and 4-(N,N-dimethylaminopyridine (DMAP, 14.39 g, 118 mmol) at room temperature. The solution was stirred at RT over night, washed with 2 N HCl and saturated aqueous sodium bicarbonate. The organic layer was dried over MgSO4, and the solvent was removed under vacuum to provide 26 g (96%) of the title compound.

Step N: Ethyl [3,5-bis(trifluoromethyl)phenyl](diazo)acetate

To a solution of ethyl 3,5-bis(trifluoromethyl)phenylacetate (Step M, 26.0 g, 87 mmol) and 4-methylbenzenesulfonyl azide (Step L, 18.0 g, 91 mmol) in dry acetonitrile (150 mL) was added DBU (14.3 mL, 95 mmol) dropwise at −10° C. over 15 min with stirring. The mixture was stirred at −10° C. for a further 0.5 hr. The solvent was removed and the residue was partitioned between ether and water. The organic layer was washed with aqueous NaHCO$_3$, brine, dried over Mg$_2$SO$_4$, and the solvent was removed. The residue was chromatographed (eluted with 9:1 hexane:ethyl acetate) to afforded a yellow solid. $^1$H-NMR (CDCl$_3$): δ: 8.0 (2H, s), 7.68 (1H, s), 4.41 (2H, d, J=7.1 Hz), 1.40 (3H, t, J=7.1 Hz).

Step O: tert-Butyl (3aR,4R,5S,7aS)-5-{(1S)-1-[3,5-bis(trifluoromethyl)phenyl]-2-ethoxy-2-oxoethoxy}-4-(2-methylphenyl)octahydro-2H-isoindole-2-carboxylate and tert-butyl (3aR,4R,5S,7aS)-5-{(1R)-1-[3,5-bis(trifluoromethyl)phenyl]-2-ethoxy-2-oxoethoxy}-4-(2-methylphenyl)octahydro-2H-isoindole-2-carboxylate To a solution of the alcohol intermediate of Step K (34 g, 105 mmol) in benzene (150 mL) at 85° C. in the presence of rhodium acetate (0.1 equiv., 2.32 g, 10.26 mmol) was added by slow addition over 8 hrs. by syringe pump, a solution of the diazoester (intermediate Step N, 45.7 g, 123 mmol) in benzene (80 mL). After completion of the reaction, solvent was removed under vacuum and the residue was purified by column chromatography (4:1 hexane:ethyl acetate) to give a product mixture of two components (45 g). M+ +1−57+1: 574.20.

Step P: tert-Butyl (3aR,4R,5S,7aS)-5-{(1S)-1-[3,5-bis(trifluoromethyl)phenyl]-2-hydroxyethoxy}-4-(2-methylphenyl)octahydro-2H-isoindole-2-carboxylate and tert-butyl (3aR,4R,5S,7aS)-5-{(1R)-1-[3,5-bis(trifluoromethyl)phenyl]-2-hydroxyethoxy}-4-(2-methylphenyl)octahydro-2H-isoindole-2-carboxylate To a solution of 2.2 g (3.57 mmol) of tert-butyl (3aR,4R,5S,7aS)-5-{(1S)-1-[3,5-bis(trifluoromethyl)phenyl]-1-(ethoxycarbonyl)methoxy}-4-(2-methylphenyl)octahydro-1H-isoindole-2-carboxylate and tert-butyl (3aS,4S,5R,7aR)-5-{(1R)-1-[3,5-bis(trifluoromethyl)phenyl]-1-(ethoxycarbonyl)}methoxy-4-(2-methylphenyl)octahydro-1H-isoindole-2-carboxylate (intermediates Step O) in 50 mL THF under nitrogen atmosphere was added LiBH$_4$ powder (0.16 g, 7.15 mmol) at 0° C. The resulting mixture was heated at 75° C. for 3 hr then cooled to RT. The reaction mixture was carefully quenched by the addition of 30 mL water at 0° C. and 30 mL saturated aqueous KHSO$_4$, then extracted with ethyl acetate. The combined organic extracts were dried over MgSO$_4$, filtered and the solvent evaporated under vacuum. The crude compounds were separated by column chromatography (eluted with 2:1 hexane:EtOAc, then 1:1 hexane:EtOAc) to afford the title compounds. The more polar isomer

EXAMPLE 2

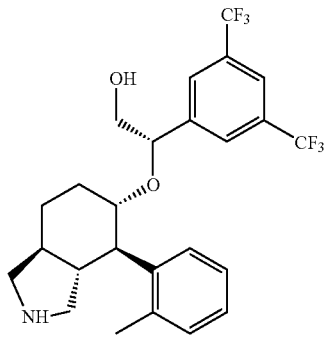

(2S)-2-[3,5-bis(trifluoromethyl)phenyl]-2-{[(3aR,4R,5S,7aS)-4-(2-methylphenyl)octahydro-1H-isoindol-5-yl]oxy}ethanol The more polar isomer (1S) isomer of EXAMPLE 1 (tert-butyl (3aR,4R,5S,7aS)-5-{(1S)-1-[3,5-bis(trifluoromethyl)phenyl]-2-hydroxyethoxy}-4-(2-methylphenyl)octahydro-2H-isoindole-2-carboxylate, 2.0 g, 3.4 mmol) was stirred in 4 N HCl in dioxane for 1 hr. The volatiles were removed, and the residue was taken into ethyl acetate. The organic layer was separated, and the aqueous was extracted with ethyl acetate. The combined organic layers were washed consecutively with 2 N NaOH, brine, dried over MgSO$_4$ and the solvent was removed to give 1.65 g of the amine title compound. M$^+$+1: 488.22

EXAMPLE 3

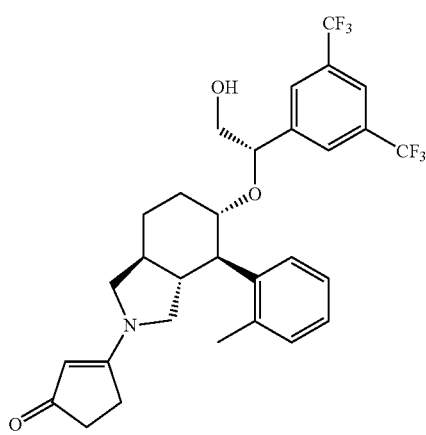

3-[(3aR,4R,5S,7aS)-5-{(1S)-1-[3,5-bis(trifluoromethyl)phenyl]-2-hydroxyethoxy}-4-(2-methylphenyl)octahydro-2H-isoindol-2-yl]cyclopent-2-en-1-one To a solution of (3aR,4R,5S,7aS)-5-{(1R)-1-[3,5-bis(trifluoromethyl)phenyl]ethoxy}-4-(2-methylphenyl)octahydro-1H-isoindole (1.65 g, 3.38 mmol, EXAMPLE 2) in 10 mL methanol was added 1 mL acetic acid. The volatiles were removed under vacuum and the residue was dissolved in 50 mL 2-propanol. The solution was heated with cyclopentadione (1.33 g, 13.54 mmol) at 80° C. overnight. The solvent was removed and the residue was taken into ethyl acetate. The solution was washed with 2 N aqueous sodium hydroxide and brine. The organic layer was dried over MgSO$_4$, and the solvent was removed. The residue was purified by column chromatography (9:1 ethyl acetate:methanol) to give 1.2 g of the title compound. $^1$H-NMR (CDCl$_3$): δ: 7.69 (1H, s), 7.16 (2H, s), 7.08-6.90 (4H, m), 4.87, 4.68 (1H, two singlets), 4.42 (1H, m), 3.70, 3.57-3.47 (3H, m), 3.17 (0.65H, m), 3.08 (0.35H, t, J=10.1 Hz), 2.98 (2H, m), 2.90 (0.65H, t, J=10.1 Hz), 2.77 (0.35H, t, J=10.1 Hz), 2.59-2.48 (2H, m), 2.42-2.33 (3H, m), 2.30 (3H, s), 2.17 (1H, m), 2.00 (2H, m), 1.65 (1H, m), 1.40 (1H, m). M$^+$+1: 568.23.

EXAMPLE 4

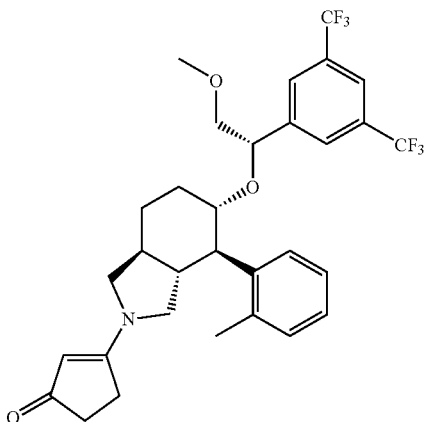

3-[(3aR,4R,5S,7aS)-5-{(1S)-1-[3,5-bis(trifluoromethyl)phenyl]-2-methoxyethoxy}-4-(2-methylphenyl)octahydro-2H-isoindol-2-yl]cyclopent-2-en-1-one The compound from EXAMPLE 3 (0.02 g, 0.035 mmol) was dissolved in DMF (15 mL) and cooled to 0° C. NaH solid (12.8 mg, 0.07 mmol) was added, and the reaction mixture was stirred at 0° C. for 5 min. A few drops of iodomethane (excess) were added to the mixture. After stirring for another 10 min at 0° C., water (1 mL) was added and the water/DMF were removed in vacuo. The residue was taken into ethyl acetate. The mixture was washed with water, dried over magnesium sulfate and concentrated. The crude material was purified by preparative TLC (10% methanol in ethyl acetate) to afford the title compound. M++1: 582.47.

EXAMPLE 5

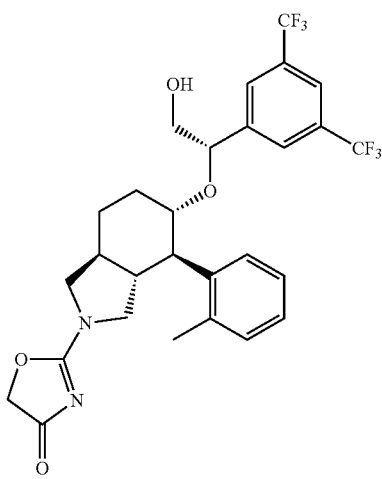

2-[(3aR,4R,5S,7aS)-5-{(1S)-1-[3,5-bis(trifluoromethyl)phenyl]-2-hydroxyethoxy}-4-(2-methylphenyl)octahydro-2H-isoindol-2-yl]-1,3-oxazol-4(5H)-one Step A: tert-butyl (3aR,4R,5S,7aS)-5-{(1S)-2-(benzoyloxy)-1-[3,5-bis(trifluoromethyl)phenyl]ethoxy}-4-(2-methylphenyl)octahydro-2H-isoindole-2-carboxylate To a solution of the (1S) isomer of EXAMPLE 1 (tert-Butyl (3aR,4R,5S,7aS)-5-{(1S)-1-[3,5-bis(trifluoromethyl)phenyl]-2-hydroxyethoxy}-4-(2-methylphenyl)octahydro-2H-isoindole-2-carboxylate, 8.61 g, 14.65 mmol) in 50 mL pyridine was added benzoyl chloride (3.40 mL, 29.3 mmol). The mixture was stirred at 50° C. for 16 hr. The volatiles were removed in vacuo. The residue was dissolved in 200 mL ethyl acetate, washed with sodium bicarbonate aqueous and brine. The organic layer was dried over $Na_2SO_4$ and concentrated in vacuo. The crude material was purified by column chromatography (EtOAc/hexane, 15% to 30% for 2900 mL, then 30% to 50% for 1250 mL) to give 10.38 g (102% yield) of the title compound. M++1: 588.1.

Step B: (2S)-2-[3,5-bis(trifluoromethyl)phenyl]-2-{[(3aR,4R,5S,7aS)-4-(2-methylphenyl)octahydro-1H-isoindol-5-yl]oxy}ethyl benzoate The intermediate from step A (8.6 g, 12.43 mmol) was added to 4 N HCl in dioxane (200 mL) at 0° C. The solution was then stirred at room temperature for 1 h. The volatiles were removed in vacuo. The residue was dissolved in 750 mL ether, washed with 2N sodium hydroxide aqueous, brine and saturated sodium bicarbonate. The organic layer was dried over $Na_2SO_4$ and concentrated in vacuo to give a foam solid (8.12 g crude). M++1: 592.49.

Step C: (2S)-2-[3,5-bis(trifluoromethyl)phenyl]-2-{[(3aR,4R,5S,7aS)-2-{[(chloroacetyl)amino]carbonyl}-4-(2-methylphenyl)octahydro-1H-isoindol-5-yl]oxy}ethyl benzoate To a solution of the intermediate from Step B (7.35 g, 12.43 mmol) in 150 mL methylene chloride was added N-(chloroloaceto)isocyanate at 0° C. The solution was stirred at rt for 1 hr, and was diluted with methylene chloride. The organic layer was separated and the aqueous layer was extracted with methylene chloride. The combined organic layers were washed with aqueous sodium bicarbonate, dried over $Na_2SO_4$ and the solvent was removed under vacuum. The off-white solid was directly used in the next step. M++1=711.1.

Step D: (2S)-2-[3,5-bis(trifluoromethyl)phenyl]-2-{[(3aR,4R,5S,7aS)-4-(2-methylphenyl)-2-(4-oxo-4,5-dihydro-1,3-oxazol-2-yl)octahydro-1H-isoindol-5-yl]oxy}ethyl benzoate A solution of the intermediate from Step C (8.84 g, 12.43 mmol) in THF (600 mL) and DBU (3.75 mL, 24.86 mmol) was heated at 50° C. for 2.5 hr. The volatiles were removed, and the crude material was purified by column chromatography [(6% methanol/EtOAc)/EtOAC 0 to 66% for 2900 mL, then 66% to 80% for 1200 mL] to give the title compound. M++1: 613.60.

Step E: 2-[(3aR,4R,5S,7aS)-5-{(1S)-1-[3,5-bis(trifluoromethyl)phenyl]-2-hydroxyethoxy}-4-(2-methylphenyl)octahydro-2H-isoindol-2-yl]-1,3-oxazol-4(5H)-one To a solution of benzoate of Step D (4.0 g, 5.93 mmol) in 200 mL of methanol was added 6.0 mL of 2 M sodium hydroxide. The reaction mixture was maintained at ambient temperature for 1 hr, and diluted with 1200 mL ether. The organic layer was washed with 1 M sodium hydroxide (400 mL). The organic layer was then washed with water, dried over $MgSO_4$, filtered, and concentrated to afford a white solid. The crude material was purified by flash chromatography (0-5% then 5-7% them 7% methanol in ethyl acetate. M++1: 571.2.

EXAMPLE 6

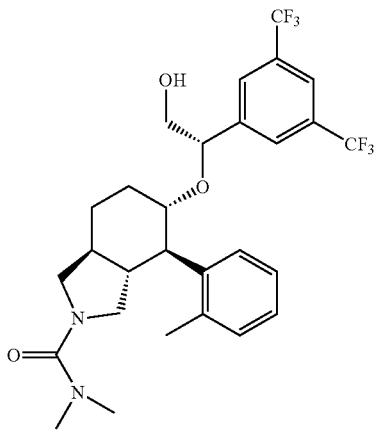

(3aR,4R,5S,7aS)-5-{(1S)-1-[3,5-bis(trifluoromethyl)phenyl]-2-hydroxyethoxy}-N,N-dimethyl-4-(2-methylphenyl)octahydro-2H-isoindole-2-carboxamide Step A: tert-Butyl (3aR,4R,5S,7aS)-5-{(1S)-1-[3,5-bis(trifluoromethyl)phenyl]-2-(acetohydroxyethoxy)}-4-(2-methylphenyl)octahydro-1H-isoindole-2-t-butylcarboxylate To a solution of the (1S) isomer of EXAMPLE 1 ((tert-Butyl (3aR,4R,5S,7aS)-5-{(1S)-1-[3,5-bis(trifluoromethyl)phenyl]-2-hydroxyethoxy}-4-(2-methylphenyl)octahydro-2H-isoindole-2-carboxylate, 1.3 g, 2.2 mmol) in methylene chloride (45 mL) was added acetyl chloride (0.26 mL, 3.32 mmol), TEA (0.93 mL, 6.64 mmol) and a catalytical amount of 4-(N,N-dimethyl)pyridine (DMAP, 0.02 g) at 0° C. The mixture was stirred at the same temperature for 1 hr. TLC showed the starting material disappeared. The reaction mixture was diluted with methylene chloride, washed with aqueous KHSO$_4$, brine, aqueous NaHCO$_3$, dried over MgSO$_4$ and the solvent was removed. The crude material was purified with by preparative TLC (1.1 g), M$^+$+1−57+1: 574.00.

Step B: (3aR,4R,5S,7aS)-5-{(1S)-1-[3,5-bis(trifluoromethyl)phenyl]-2-(acetohydroxyethoxy)}-4-(2-methylphenyl)octahydro-1H-isoindole The above compound (Step A, 1.1 g, mmol) in 15 mL 4 N HCl in dioxane was stirred for 1 hr. The volatiles were removed under vacuum in 40° C. water bath. The residue was dissolved in ethyl acetate. The solution was washed with NaHCO$_3$ aqueous, brine, dried over MgSO$_4$, and the solvent was removed to give 0.85 g. The compound was kept in freezer. M$^+$+1: 532.02.

Step C: (3aR,4R,5S,7aS)-5-{(1S)-1-[3,5-bis(trifluoromethyl)phenyl]-2-hydroxyethoxy}-N,N-dimethyl-4-(2-methylphenyl)octahydro-2H-isoindole-2-carboxamide To a solution of the above compound (Step B, 0.13 g, 0.25 mmol) in 25 mL methylene chloride were added N,N-dimethyl chloroformide (0.03 mL, 0.33 mmol), triethyl amine (0.055 mL, 0.040 mmol) and a catalytical amount of DMAP at room temperature. The mixture was stirred at the same temperature for 1 hr. The solvent was removed and the residue was heated with 10 mL 2 N NaOH in 40 mL methanol at 50° C. for 1 hr. Methanol was removed under vacuum. The residue was diluted with water, and the aqueous was extracted with ethyl acetate. The organic layers were washed with brine, dried (MgSO4) and the solvent was removed. The residue was purified by preparative TLC (95:5 EtOAc:methanol), 0.07 mg. M$^+$+1: 559.04.

EXAMPLE 7

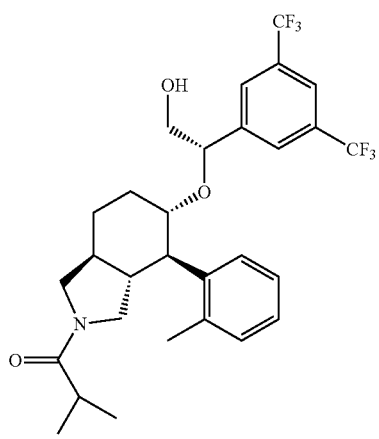

(2S)-2-[3,5-bis(trifluoromethyl)phenyl]-2-{[(3aR,4R,5S,7aS)-2-isobutyryl-4-(2-methylphenyl)octahydro-1H-isoindol-5-yl]oxy}ethanol To a solution of the compound from EXAMPLE 2 in CH$_2$Cl$_2$ was added isobutyric chloride, triethylamine and a catalytic amount of DMAP. The mixture was stirred at room temperature for 2 hr. The solvent was removed and the residue was heated with 10 mL 2 N NaOH in 40 mL methanol at 50° C. for 1 hr. Methanol was removed under vacuum. The residue was diluted with water and the aqueous was extracted with ethyl acetate. The organic layer was washed with brine, dried (MgSO$_4$) and the solvent was removed. The residue was purified by preparative TLC (80:20 EtOAc:hexane), 0.07 mg. M+1: 558.16.

Using the procedures essentially comparable to those described above the compounds of the following Examples were prepared.

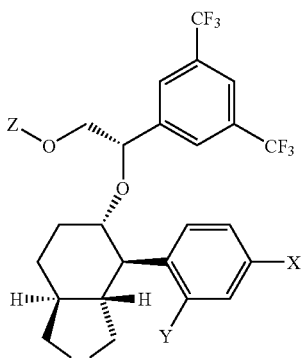

| Ex. # | R$^1$ | X | Y | Z | parent ion (MH$^+$) m/z |
|---|---|---|---|---|---|
| 8 | 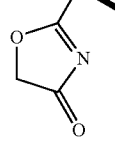 | F | H | H | 575.4 |
| 9 | 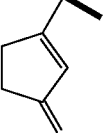 | F | H | H | 572.2 |
| 10 | 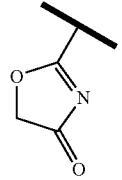 | F | CH$_3$ | H | 589.6 |
| 11 | 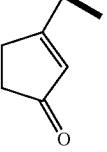 | F | CH$_3$ | H | 586.1 |
| 12 | 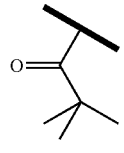 | H | CH$_3$ | H | 572.4 |
| 13 | 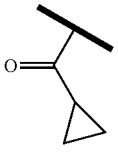 | H | CH$_3$ | H | 556.2 |

-continued

Table for structure 29 (Z-O-CH2-CH(3,5-bis-CF3-phenyl)-O- on bicyclic pyrrolidine with aryl bearing X, Y):

| Ex. # | R¹ | X | Y | Z | parent ion (MH⁺) m/z |
|---|---|---|---|---|---|
| 14 | -CH(CH₃)C(O)N(CH₃)₂ | H | CH₃ | CH₃ | 573.4 |
| 15 | -CH(CH₃)C(O)OC(CH₃)₃ | F | H | H | 536.3 (M⁺ + 1 − 56) |
| 16 | H | F | H | H | 492.2 |
| 17 | H | H | CH₃ | C₆H₅CO | 592.4 |
| 18 | 2-(4-oxo-4,5-dihydrooxazol-2-yl) | H | CH₃ | CH₃CO | 613.3 |
| 19 | 2-(4-oxo-4,5-dihydrooxazol-2-yl) | H | CH₃ | C₆H₅CO | 675.4 |
| 20 | -CH(CH₃)C(O)OC(CH₃)₃ | H | CH₃ | C₆H₅CO | 636.5 (M⁺ + 1 − 56) |

Table for structure 30:

| Ex. # | R¹ | X | Y | Z | parent ion (MH⁺) m/z |
|---|---|---|---|---|---|
| 21 | 3-oxocyclopent-1-enyl | F | H | H | 572.3 |
| 22 | H | H | CH₃ | H | 488.2 |
| 23 | 3-oxocyclopent-1-enyl | H | CH₃ | H | 568.2 |
| 24 | -CH(CH₃)C(O)C(CH₃)₃ | H | CH₃ | H | 572.4 |
| 25 | -CH(CH₃)C(O)N(CH₃)₂ | H | CH₃ | H | 559.0 |
| 26 | -CH(CH₃)C(O)OC(CH₃)₃ | F | H | H | 536.3 (M⁺ + 1 − 56) |
| 27 | H | F | H | H | 492.2 |

What is claimed is:

1. A compound of the formula I:

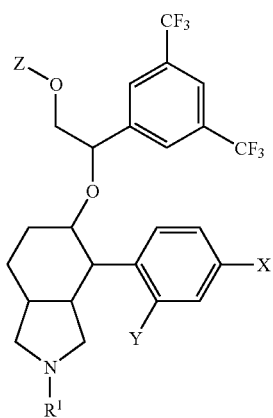

I or a pharmaceutically acceptable salt thereof and individual enantiomers and diastereomers thereof wherein: $R^1$ is

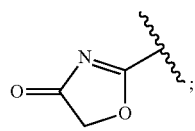

X is independently selected from the group consisting of:
(1) hydrogen, and
(2) fluorine;
Y is independently selected from the group consisting of:
(1) hydrogen, and
(2) methyl; and
Z is independently selected from the group consisting of:
(1) hydrogen,
(2) $C_{1-6}$alkyl, which is unsubstituted or substituted with halogen, hydroxyl or phenyl,
(3) —(CO)—$C_{1-6}$alkyl,
(4) —(CO)-Aryl,
(5) —(CO)O—$C_{1-6}$alkyl,
(6) —(CO)—$NH_2$,
(7) —(CO)—$NHC_{1-6}$alkyl, and
(8) —(CO)—$N(C_{1-6}$alkyl)($C_{1-6}$alkyl).

2. The compound of claim 1 of the formula Ia or Ib:

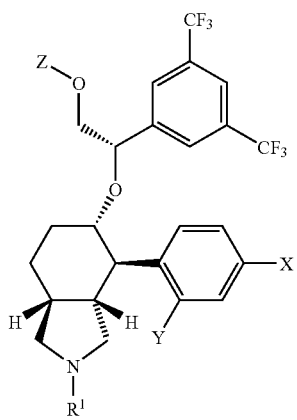

Ia

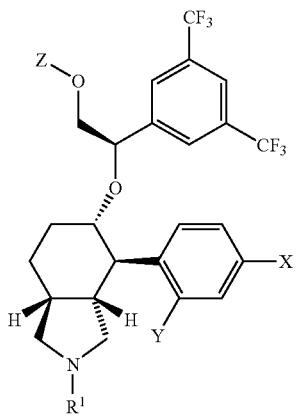

Ib or a pharmaceutically acceptable salt thereof and individual enantiomers and diastereomers thereof.

3. The compound of claim 2 of the formula Ia:

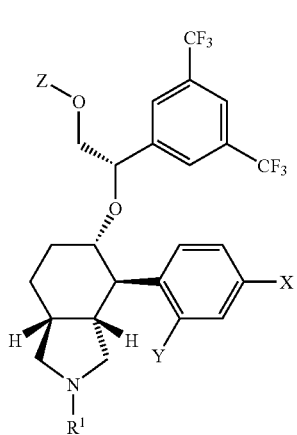

Ia or a pharmaceutically acceptable salt thereof and individual enantiomers and diastereomers thereof.

4. The compound of claim 2 of the formula Ib:

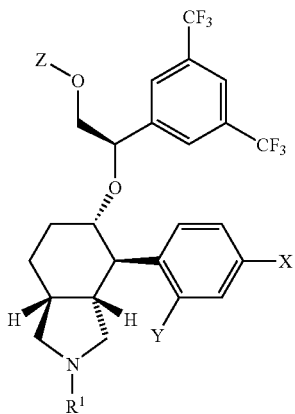

or a pharmaceutically acceptable salt thereof and individual enantiomers and diastereomers thereof.

5. The compound of claim 1 wherein Z is selected from the group consisting of (1) hydrogen,
(2) $C_{1-3}$alkyl, which is unsubstituted or substituted with halogen, hydroxyl or phenyl,
(3) —(CO)-phenyl, and
(4) —(CO)O-methyl.

6. The compound of claim 1 wherein X is hydrogen.
7. The compound of claim 1 wherein X is fluorine.
8. The compound of claim 1 wherein Y is hydrogen.
9. The compound of claim 1 wherein Y is methyl.
10. The compound of claim 1 wherein Z is hydrogen.
11. The compound of claim 1 wherein Z is methyl.
12. The compound of claim 1 of the formula Ia or Ib:

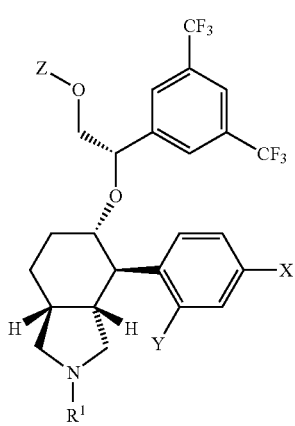

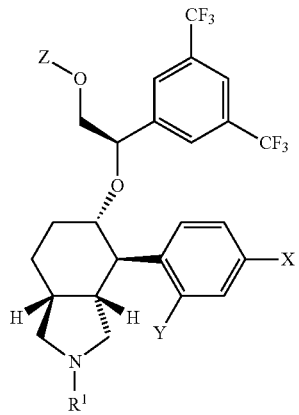

or a pharmaceutically acceptable salt thereof and individual enantiomers and diastereomers thereof wherein $R^1$ is

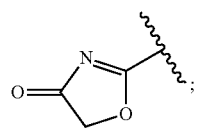

X is independently selected from the group consisting of:
(1) hydrogen, and
(2) fluorine;

Y is independently selected from the group consisting of:
(1) hydrogen, and
(2) methyl; and Z is independently selected from the group consisting of:
(1) hydrogen,
(2) $C_{1-6}$alkyl, which is unsubstituted or substituted with halogen, hydroxyl or phenyl,
(3) —(CO)—$C_{1-6}$alkyl,
(4) —(CO)-Aryl,
(5) —(CO)O—$C_{1-6}$alkyl, and
(6) —(CO)—$NH_2$.

13. A compound of claim 12 wherein Z is selected from the group consisting of (1) hydrogen,
(2) $C_{1-3}$alkyl, which is unsubstituted or substituted with halogen, hydroxyl or phenyl,
(3) —(CO)-phenyl, and
(4) —(CO)O-methyl.

14. A compound of claim 12 wherein Z is selected from hydrogen and methyl.

15. A compound which is selected from the group consisting of:

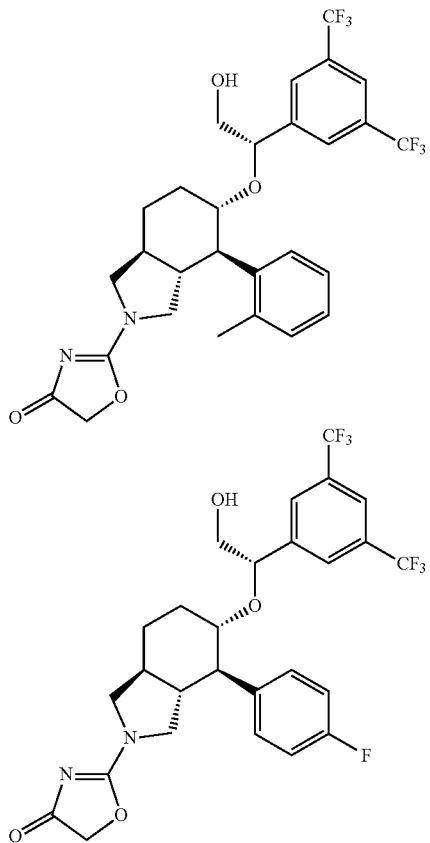

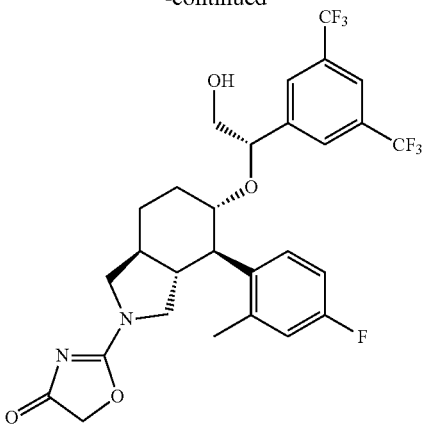

and pharmaceutically acceptable salts thereof.

16. A pharmaceutical composition which comprises an inert carrier and a compound of claim 1.

17. A method for the treatment of pain or inflammation, migraine, emesis, post-therapeutic neuralgia, depression, anxiety or urinary incontinence, and LUTS which method comprises administration to a patient in need thereof a therapeutically effective amount of the compound of claim 1.

18. A method according to claim 17 for the treatment of urinary incontinence or LUTS.

19. A method of antagonizing the effect of substance P at its receptor site or for the blockade of neurokinin-1 receptors in a patient in need thereof comprising administration to said patient a therapeutically effective amount of the compound of claim 1.

* * * * *